(12) United States Patent
Ollivier et al.

(10) Patent No.: US 10,874,852 B2
(45) Date of Patent: *Dec. 29, 2020

(54) INTRACARDIAC CAPSULE AND EXPLANTATION ACCESSORY

(71) Applicant: SORIN CRM SAS, Clamart (FR)

(72) Inventors: Jean-François Ollivier, Gif sur Yvette (FR); Philippe D'hiver, Châtillon (FR); Willy Regnier, Longjumeau (FR)

(73) Assignee: Sorin CRM SAS, Clamart (FR)

( * ) Notice: Subject to any disclaimer, the term of this patent is extended or adjusted under 35 U.S.C. 154(b) by 126 days.

This patent is subject to a terminal disclaimer.

(21) Appl. No.: 16/184,969

(22) Filed: Nov. 8, 2018

(65) Prior Publication Data

US 2019/0070408 A1  Mar. 7, 2019

Related U.S. Application Data

(63) Continuation of application No. 14/680,832, filed on Apr. 7, 2015, now Pat. No. 10,124,163.

(30) Foreign Application Priority Data

Apr. 8, 2014 (FR) ...................................... 14 53132

(51) Int. Cl.
*A61N 1/05* (2006.01)
*A61N 1/375* (2006.01)
(Continued)

(52) U.S. Cl.
CPC ........... *A61N 1/0573* (2013.01); *A61N 1/059* (2013.01); *A61N 1/372* (2013.01); *A61N 1/3756* (2013.01);
(Continued)

(58) Field of Classification Search
None
See application file for complete search history.

(56) References Cited

U.S. PATENT DOCUMENTS

| 2008/0086168 A1 | 4/2008 | Cahill |
| 2009/0163926 A1 | 6/2009 | Sos |
| 2012/0165827 A1 | 6/2012 | Khairkhahan |

FOREIGN PATENT DOCUMENTS

| EP | 2 394 695 A1 | 12/2011 |
| EP | 2 818 202 | 12/2014 |
| WO | WO-2012/082755 | 6/2012 |

OTHER PUBLICATIONS

Preliminary Search Report for French Patent Application No. FR 1453132, dated Oct. 10, 2014, 1 page.

*Primary Examiner* — Shaun L David
(74) *Attorney, Agent, or Firm* — Foley & Lardner LLP

(57) ABSTRACT

An autonomous capsule includes a tubular body provided at its distal end with an anchoring screw, and in its proximal region of a capture groove. An explantation accessory includes a reinforced catheter combined with a flexible wire which can slide in the catheter and has a deformable loop which can be clamped by gradual introduction of its ends in the catheter under the effect of a traction exerted on the wire. During tightening, the capture groove receives the wire loop, allowing, after complete tightening, to secure in tension and rotation an assembly formed by the catheter, the capsule, and the wire. The reinforced catheter is then used to transmit a tensile force and an axial torque from its proximal end to its distal end, allowing safe unscrewing of the capsule and its extraction through the patient venous network.

20 Claims, 4 Drawing Sheets

(51) Int. Cl.
*A61N 1/372* (2006.01)
*A61M 25/00* (2006.01)
(52) U.S. Cl.
CPC ..... *A61N 1/37518* (2017.08); *A61M 25/0012* (2013.01); *A61M 25/0082* (2013.01); *A61M 2025/0059* (2013.01); *A61N 1/37205* (2013.01); *A61N 2001/0578* (2013.01)

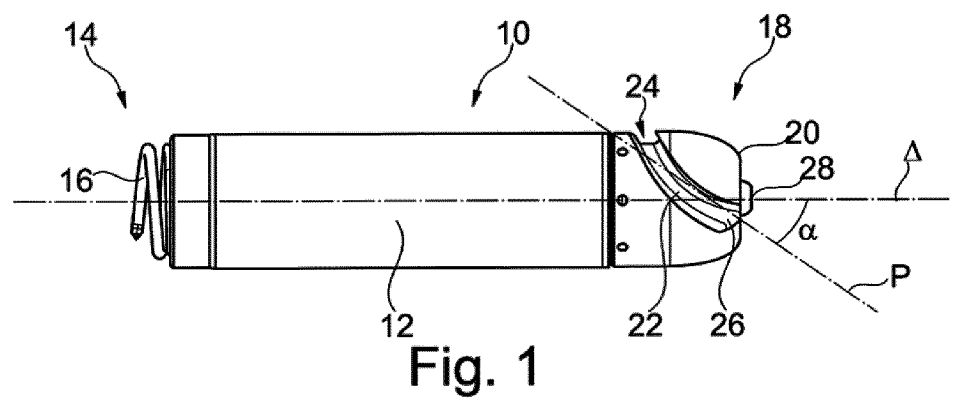
Fig. 1
Fig. 1a
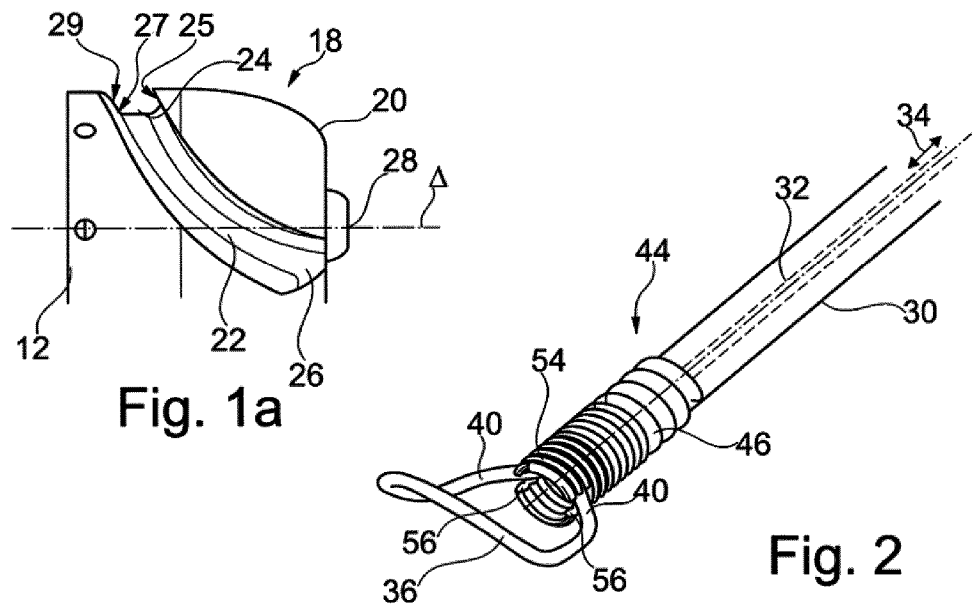
Fig. 2
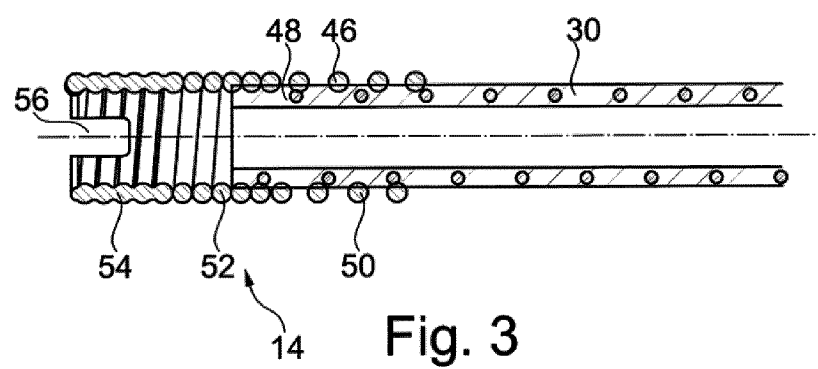
Fig. 3

INTRACARDIAC CAPSULE AND EXPLANTATION ACCESSORY

CROSS REFERENCE TO RELATED APPLICATIONS

This application is a continuation of U.S. patent application Ser. No. 14/680,832, filed Apr. 7, 2015, which claims the benefit of and priority to French Patent Application No. 1453132, filed Apr. 8, 2014, both of which are hereby incorporated by reference in their entirety.

BACKGROUND

The invention relates to "active implantable medical devices" as defined by Directive 90/385/EEC of 20 Jun. 1990 of the Council of the European Communities, particularly to devices that continuously monitor heart rhythm and deliver, if needed, electrical stimulation, resynchronization and/or defibrillation pulses to the heart in case of arrhythmia detected by the device. It relates more particularly, but is not limited to, the explantation of those devices which are provided at the distal end with an anchor member such as a helical screw, axially extending from the body of the device and intended to enter the heart tissue by screwing at the selected implantation site.

The invention relates especially, but is not limited to, those devices that are in the form of an autonomous capsule intended to be implanted in a heart chamber (atrium or ventricle, right or left). These capsules are free of any mechanical connection to an implanted (such as the housing of the stimulation pulse generator) or non-implanted (external device such as a programmer or a monitoring device for remote patient monitoring) main device. For this reason these capsules are called "leadless capsules," to distinguish them from the electrodes or sensors disposed at the distal end of a conventional probe (lead), which is traversed throughout its length by one or more conductors galvanically connecting the electrode or sensor to a generator connected to an opposite, proximal end of the probe. Note, however, that the autonomous nature of the capsule is not inherently a mandatory feature of the invention.

The explantation of these autonomous capsules is a particularly delicate operation because it is necessary, first, to manage to capture the body of the capsule using an explantation accessory and, second, to exercise in this body a torque for detaching it from the implantation site wherein it was retained by the anchoring screw. This unscrewing torque must be large enough to overcome resistance and adhesions resulting from the formation of fibrous tissue at the location of the implantation site.

In the case of endocardial capsules (that is to say capsules attached to the inner wall of an atrial or ventricular chamber, as opposed, for example, to the epicardial capsules secured to the outer wall of the heart), the explantation constraints are increased due to, first, the need to go through the peripheral venous system to introduce the explantation accessory and, second, the need to remove the capsule after it was caught and unscrewed while ensuring its withdrawal through the tight curves of the venous system. These maneuvers must be performed both accurately and in a completely secure method.

Some explantation accessories designated as "lassos" or snares are known, and are commonly used to capture and remove medical devices such as a probe body, defective catheters, guides, etc., out of the heart chambers or out of the venous system. These lassos may include a flexible wire terminated at its distal end by a deformable loop of shape memory metal, the loop extending in the free state in a plane generally perpendicular to the wire plane which supports it. The wire is introduced into the distal opening of a catheter, crossing through it to emerge proximally. The tension of the wire from the proximal end of the catheter has the effect, at the other end, to pull on the loop while progressively making it enter into the catheter wherein it will be housed.

The catheter is introduced into the patient's body, with the fully folded loop in the distal end region. The loop is then deployed from the catheter by pushing the wire from the proximal end. Because of the shape memory of the metal, the loop then recovers its inclined lasso shape relative to the direction of the wire and of the catheter. The lasso can be oriented at will to capture the element to be extracted. Pulling on the wire then allows to partially enter the loop in the catheter, which has the effect of reducing the size and thus to ensure clamping of the element to be removed.

These accessories have the advantage of having a small introduction diameter (from about 2 to 6 Fr, 0.66 to 2 mm), while having a high capture diameter (typically about 10 to 30 mm).

However, in the envisaged application including unscrewing a device such as a capsule screwed into a wall, these accessories are not suitable because they do not transmit significant torque, while to extract a screwed capsule it is necessary to exercise up to 1 N·cm to this capsule. In addition, this unscrewing torque must be substantially exerted in the axis of the capsule.

However, with a conventional lasso accessory, the catheter used to control the size of the loop of the lasso tends to move perpendicular to the element captured by the lasso (that is to say that the axis of the element is oriented perpendicularly to the direction of the catheter), at best parallel to a generatrix of the element. However, in such a configuration any unscrewing action would cause a twisting of the tissue around the fastening screw, without a significant unscrewing effect and with a high risk of tamponade.

Finally, this capturing mode wherein the elongated body of an autonomous capsule would be oriented perpendicular to the catheter axis (the assembly thus taking the form of a T) would be completely incompatible with fully secured retrieval across the venous network.

WO 2012/082755 A1 discloses an explantation accessory for leadless capsule, including one or more lassos capturing a body formed in the posterior portion of the capsule, such as a button, or projecting spouts or hooks. The docking body of the catheter includes a receptacle which fits on the rear portion of the capsule after the latter has been captured by the lasso(s), so as to transmit unscrewing torque required for explantation. This structure, however, is relatively mechanically complex, and furthermore it does not solve the difficulty of the capture maneuver by the lasso, which is to capture very small size spouts or hooks.

US 2009/0163926 A1 describes a lasso catheter for explantation of angeiology devices such as filters inserted in veins, wherein the problem of transmission of a relatively important unscrewing torque does not arise at all.

SUMMARY

To overcome these drawbacks, the invention proposes, firstly, a specific explantation accessory made from known elements but until now used in different contexts and, secondly, to develop on the capsule body a capture groove or an analog member for directing the loop of the lasso to a point near the axis of the capsule.

More specifically, the invention provides an assembly that includes, for example, as disclosed in WO2012/082755 A1 above:

an autonomous capsule, including a tubular body provided at its distal end with a screwing anchoring member adapted to penetrate into a tissue of a wall of an organ of a patient; and an explantation accessory including a catheter and a lasso including a flexible wire mobile in translation in the catheter and provided at its distal emerging end of a deformable loop, said loop being adapted to be clamped by gradual introduction of its ends in the catheter under the effect of a traction exerted on the flexible wire;

the catheter is a reinforced catheter adapted to transmit a tensile load and an axial torque from its proximal end to its distal end; and in its proximal region, the capsule includes a capture member adapted to receive the loop of the lasso during the clamping thereof and able to exert a pull and a rotation effort on the assembly formed by the catheter, the capsule and the lasso after clamping of this loop.

In a certain characteristic of the invention, the capture member includes at least one capture groove formed on the proximal end region of the capsule, the groove extending along a curvilinear outline globally oriented in an oblique plane relative to the axis of the tubular body, and this contour being an open profile whose two ends open proximally in the neighborhood of an axial end point of the tubular body.

According to various advantageous embodiments:

the oblique plane according to which the curvilinear contour of the capture groove is oriented forms an angle of between 30° and 60° relative to the axis of the tubular body;

the capture groove is symmetrical with respect to a longitudinal axial plane of the tubular body;

the profile of the cross section of this capture groove has a proximally against undercut angle;

the assembly includes two diametrically opposed symmetrical capture grooves with respect to the axis of the tubular body;

the in the depth and width dimensions of the groove are between 1 and 3 times the diameter of the flexible wire of the lasso in the loop region;

the reinforced catheter carries at its distal end a specific tip with a rigid distal tip portion extending of the catheter beyond its distal end, and a proximal tip portion mounted on the catheter and elastically deformable so as to provide degrees of freedom in axial deflection of the rigid distal tip portion;

this rigid distal tip portion includes symmetric notches for receiving ends of the loop of the lasso;

the above-mentioned specific tip is a helical spring successively including a first series of coils gripping the distal end of the catheter and forming the rigid distal tip portion, a second series of turns extending beyond the distal end of the catheter and forming the proximal tip portion, and a third series of turns at the free end of the spring with contiguous turns and symmetrical grooves for receiving the ends of the loop of the lasso; and the assembly includes, in addition to the autonomous capsule and to the explantation accessory, a remotely guidable catheter adapted to receive the armed lasso catheter with the wire inserted therein, this remotely guidable catheter including at its distal end a protective tubular tip defining an internal volume sized to be able to accommodate the capsule after explantation.

The invention also relates, considered independently, to i) the capsule of this assembly, provided with the capture member in the proximal portion, and to ii) the explant accessory of this assembly, suitable for the extraction of such a capsule.

DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is a side view of an intracardiac leadless capsule according to an embodiment of the invention, with a capture groove.

FIG. 1a is a partial enlarged view of FIG. 1, showing detail of the proximal region of the capsule.

FIG. 2 is a perspective view of the distal end of the explant accessory according to the invention, with a reinforced catheter with its specific tip wherein a capture lasso has been introduced.

FIG. 3 is a longitudinal sectional view of the distal end of the reinforced catheter of the accessory of FIG. 2, without the lasso.

DETAILED DESCRIPTION

Figure 4:
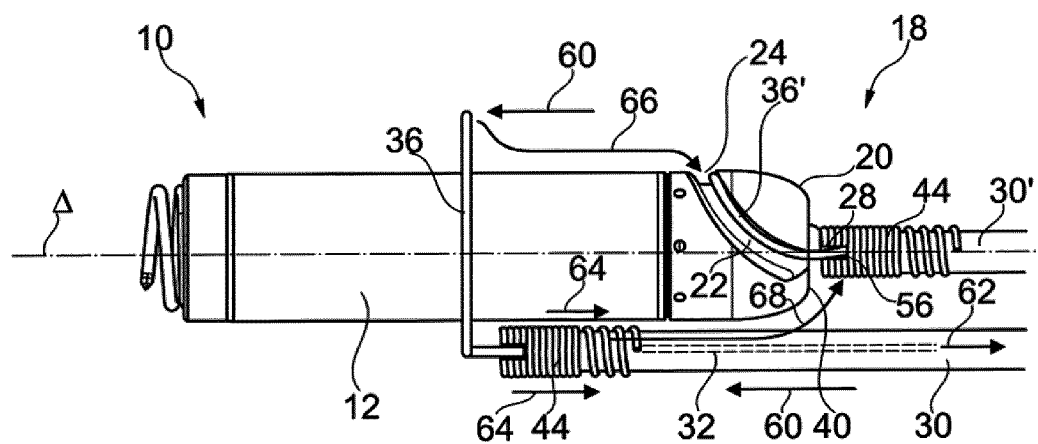
FIG. 4 is a side view showing the capsule of FIG. 1, with the explant accessory shown in two successive operating positions, respectively at the beginning and at the end of the fastening maneuver of the accessory with the capsule.

An embodiment of the capsule of the invention is shown on FIGS. 1, 1a, 4 and 5. In these figures, the numeral reference 10 generally designates the capsule, formed as a cylindrical tubular body 12 along axis Δ enclosing the various electronic and power supply circuits of the capsule. Typical dimensions of such a capsule is a diameter of the order of 6 mm to a length of about 25 mm. At its distal end 14, the capsule includes a helical anchoring screw 16 for fixing it into the tissue, for example against a wall of a heart chamber. This screw can optionally be an active, electrically conductive screw for collecting potential of cardiac depolarization and/or for the application of stimulation pulses.

The proximal region 18 of the capsule 10 preferably has a rounded, atraumatic end 20 and it is provided with a capture member which is used during explantation of the capsule. In the embodiment illustrated in FIGS. 1, 1a, 4 and 5, the capture element includes a capture groove 22. This groove extends along a curvilinear contour in the approximate shape of a horseshoe, overall oriented in an oblique plane P with respect to the axis Δ of the tubular body, the plane P typically forming an angle α between 30° and 60° relative to the axis Δ. The curvilinear contour of the groove 22 is symmetrical with respect to a longitudinal axial plane of the tubular body (plane containing Δ). The contour of the capture groove 22 is, in the illustrated example, a unique, open, shape with a central region 24 from which two arms extend in a proximal direction, said arms being oriented approximately in the plane P, with the ends 26 of each arm located near an axial end point 28 of the capsule. The dimensions in width and depth of the capture groove 22 are in the order of one to three times the diameter of the flexible wire loop of the lasso to be used for the explantation of the capsule (see below).

Note that the profile of the cross section of the capture groove 22 is substantially constant over the entire curved edge of the capture groove. This profile presents on its proximal side an angle against undercut (reference 25 in FIG. 1a), while at the distal side, it is inclined in a gentle slope (reference 27 in FIG. 1a) for connection to the tubular body 12 (radius of curvature referenced 29 in FIG. 1a).

FIG. 2 illustrates the specific explantation accessory of the assembly according to the invention shown in isolation in the closed position of the loop (that is to say corresponding to the configuration of the loop 36' of FIGS. 4 and 5), the capsule being hidden in this FIG. 2. This accessory includes a catheter 30 which, characteristically of the invention, is a reinforced catheter, thus capable of transmitting, over its entire length and to its distal end, both a pulling force and a rotation axial torque, both exerted from the proximal end of the catheter. A JR4 catheter model diameter of 5 French (1.66 mm) of the company Cordis may for example be used, modifying this catheter to add to it a specific nozzle 44 as described below with reference to FIGS. 2 and 3.

Figure 5:
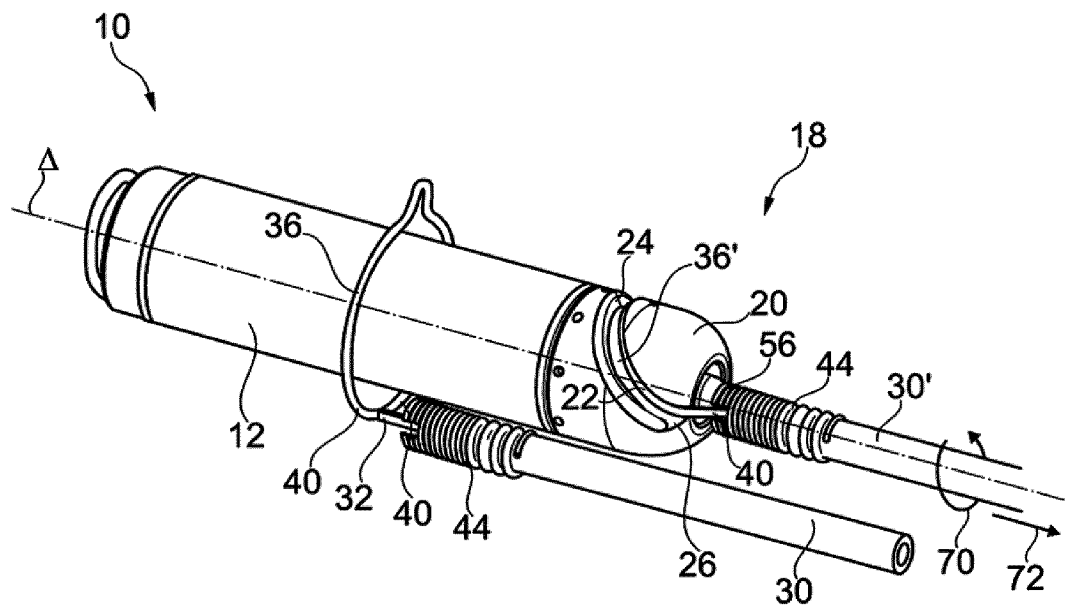
FIG. 5 is similar to FIG. 4, in perspective view.

The inner lumen 30 houses a flexible wire 32 movable in translation inside (arrow 34) and terminated at its distal end by a loop 36. This loop extends, in the free state, in a plane substantially perpendicular to the direction of the flexible wire 32 (as seen in FIGS. 4 and 5). From this free state, if a proximal pull is exerted on the flexible wire 32, both ends of the loop 40 will be gradually drawn and introduced into the catheter 30 (configuration shown in FIG. 2), resulting in a gradual reduction in the perimeter of the loop 36 giving the sought effect of "lasso." The maneuver is obviously reversible, allowing loosening of the loop and repositioning of the lasso.

The loop is made of a shape memory alloy such as nitinol allowing the lasso to regain its rounded loop and orientation perpendicular to the flexible wire once the loop of the catheter tip is completely emerged.

A lasso (snare) such as the GN2000 Gooseneck of the Covidien company, with a loop diameter of 10 to 30 mm, may be used for example, the dimension being adapted to the capture of the tubular body of an intracardiac capsule of a diameter of about 6 mm. This lasso is however not used with its original catheter, which is a flexible catheter, but in combination with a reinforced catheter, as described above.

In FIGS. 2 and 3, a specific nozzle 44 is illustrated which has been provided with the catheter 30. The function of this tip is to achieve with the assembly reinforced catheter 30 and lasso 36 the particular maneuver of explantation with unscrewing of the element to be extracted. This specific tip 44 essentially includes a rigid portion located beyond the distal end of the catheter and connected thereto by an elastically deformable flexible portion to provide degrees of pivotal freedom (axial bending) between the rigid portion and the tip of the catheter.

In the embodiment illustrated in FIGS. 2 and 3, this specific nozzle 44 is formed by winding a spring 46 on the distal end 48 of the catheter 30. The proximal portion 50 of the spring 46 is made of non-contiguous turns and provides a snug fit on the distal end 48 of the catheter, preferably with an additional direct gluing of the spring on the catheter between the turns. The proximal portion 50 is extended beyond the catheter by a median portion 52 with contiguous, not welded together, turns so as to form an resilient hinge such as a ball joint between the proximal portion 50 and a distal portion of end 54, with contiguous turns stiffened together by laser. Welding the distal portion 54 is then functionally equivalent to a rigid cylinder articulated to the end 48 of the catheter through the turns of the median portion 52. The rigid portion of the distal end 54 of the tip 44 further includes two diametrically opposed notches 56 whose width and depth are slightly greater than the diameter of the wire of the loop 36 of the lasso, so as to receive and guide the ends of the loop 40 at the clamping of the latter.

Note that the resilient hinge such as a ball joint may be achieved by other methods than the helical spring element that was just described. Thus, an alternative method includes machining a cylindrical part with a solid wall by laser cutting to form the end recesses 56, and in an intermediate region of the side wall one or more helical grooves which give to the part in this area the required axial bending elasticity.

Figure 6:
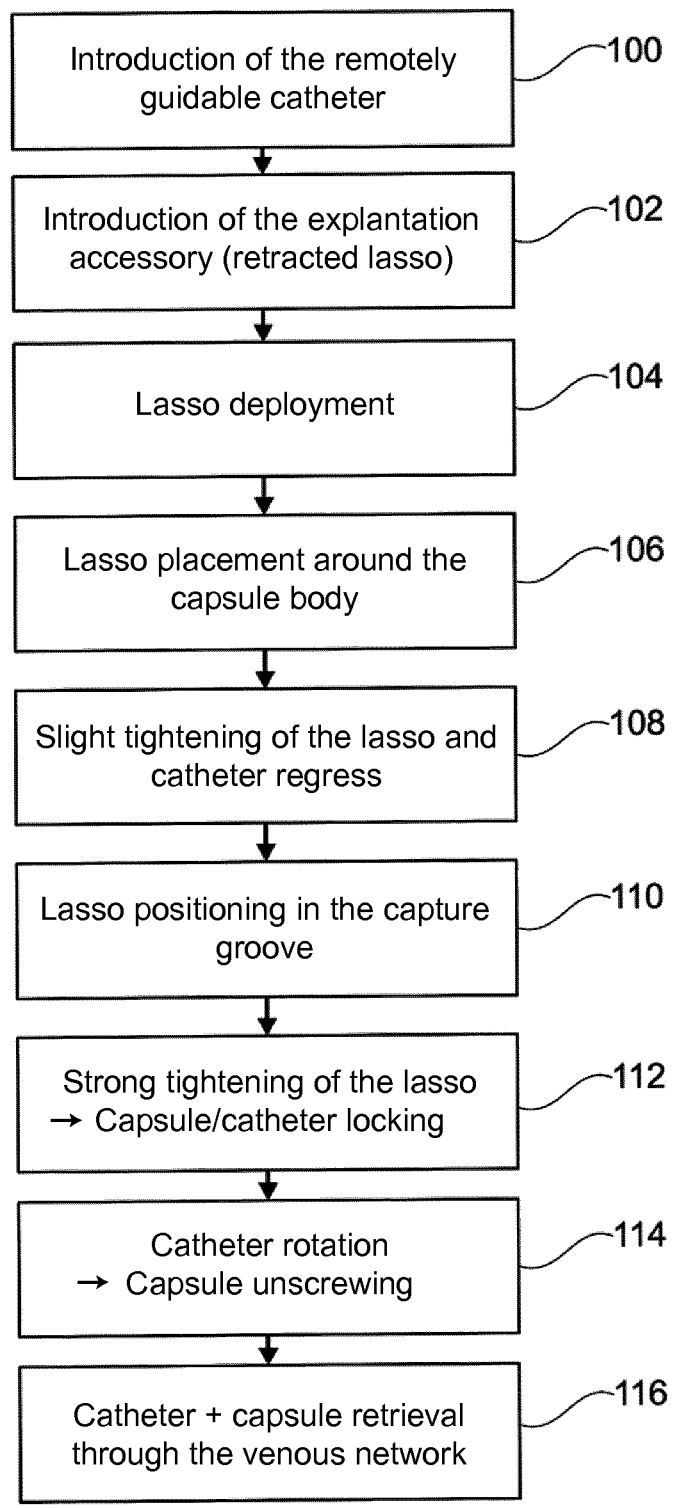
FIG. 6 is a flowchart of the successive steps of an explantation method using the accessory of the invention.

With reference to FIGS. 4 and 5, the method of explantation of an intracardiac capsule of the type described above (or of a similar device) will now be described. This method is illustrated by steps 100-116 of the flowchart of FIG. 6.

If the capsule is implanted, for example into the right ventricle, the first step is to introduce into a femoral vein a remotely adjustable catheter to create a pathway to the heart chamber (Step 100). The explantation accessory is then introduced by this pathway, with the loop 36 of the lasso in a retracted position within the reinforced catheter 30 (step 102). The loop 36 is then deployed by pushing the flexible wire 32 (Step 104) and the lasso is manipulated to be placed around the tubular body 12 (Step 106), as illustrated at 36 in FIGS. 4 and 5 (arrows 60).

The diameter of the loop 36 of the lasso is then reduced by exerting on the wire 32 a traction in the proximal direction (arrow 62), while leaving sufficient space between the loop 36 of the lasso and the tubular body 12 to allow it to slide on the latter (step 108). During tightening of the loop, the lasso is slightly inclined relative to the axis of the capsule body, and the progressive longitudinal decline of the catheter (arrows 64) with maintaining of the lasso clamping force allows the loop 36 to slightly be inclined relative to the axis of the tubular body 12 and backward (rightward in FIGS. 4 and 5) until the loop enters into the capture groove 22 in the region of the central part 24 of this groove (step 110). This transition of the loop 36 from the center of the tubular body toward the proximal region of the capsule wherein the capture groove 22 is located is illustrated by arrows 66 and 68 in FIG. 4.

The continuation of the movement, combined with maintenance of the clamping force, allows entire positioning of the lasso in the groove, as shown at 36' in FIGS. 4 and 5, the catheter end with the specific tip 44 then being positioned behind the capsule and substantially along its axis, with between the axis Δ of the tubular body 12 and the axis of the catheter 30' a distance not greater than 0-3 mm.

The maneuver can be facilitated by slightly rotating the reinforced catheter 30 to place the arms 40 of the lasso in the notches 56 of the tip. After fluoroscopic control of a minimum angle between the capsule and the reinforced catheter confirming the proper placement of the lasso in the groove, strong clamping force is then applied by the practitioner to lock the assembly capsule 10, lasso 36' and reinforced catheter 30' (step 112).

Note that the profile of the capture groove 22 actively participates in the holding of the loop, which is under significant tension in the groove, because of the angle against undercut, proximal side (reference 25 in FIG. 1a). Conversely, the sliding of the loop toward the bottom of the groove is aided by the inclined plane 27 and the proximal connection radius 29 of the groove profile.

The resulting assembly is then secured in traction, and also in rotation through the placement of the arms 40 of the lasso loop in the slots 56. The ability of the reinforced catheter 30' to transmit axial torque (arrow 70) is then used to apply an unscrewing torque directly to the capsule, the lasso body (the flexible wire 32) being only subjected to traction effort during this step. The capsule can then be detached from the wall wherein it was screwed (step 114).

The explant is then completed by axial traction (arrow 72) on the reinforced catheter 30' and by removing the capsule through the venous system (step 116). Note that, although it is highly resistant to traction, the assembly capsule 10, lasso 36 ' and reinforced catheter 30' is flexible in all directions in the longitudinal plane (plane containing the axis Δ of the capsule) due to the articulation provided by the central region 52 of the tip 44. This property facilitates the transition from tight bends and thus the drive back into the venous system. A second articulation effect in the longitudinal plane is achieved by the rigid contact under pressure, due to the traction on the lasso, between the distal side of the tip 44 and the axial end point 28 of the capsule.

It is possible to use as a delivery catheter (catheter for creating the access route to the heart chamber) a remotely adjustable catheter having at its distal end a tubular protection end, as described for example in the French application FR 1356020 of Jun. 24, 2013 (published as EP2818202 (A1)) entitled "a coupling system between a medical device and its implantation accessory." This tip, located in an approach region remote in the proximal direction from the implantation site, will receive and house the capsule after explantation and removal thereof to the tip, so that the final path of extraction in the venous system may be performed while protecting the vessel walls from the sharp end of the anchoring screw 16.

Figure 7:
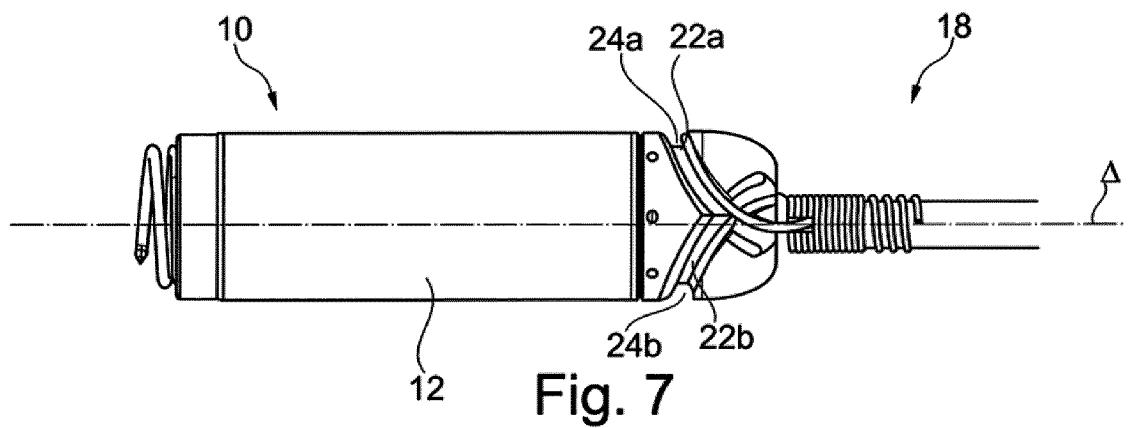
FIG. 7 illustrates the capsule of the embodiment of FIG. 1, with two diametrically opposite identical capture grooves.
Figure 8:
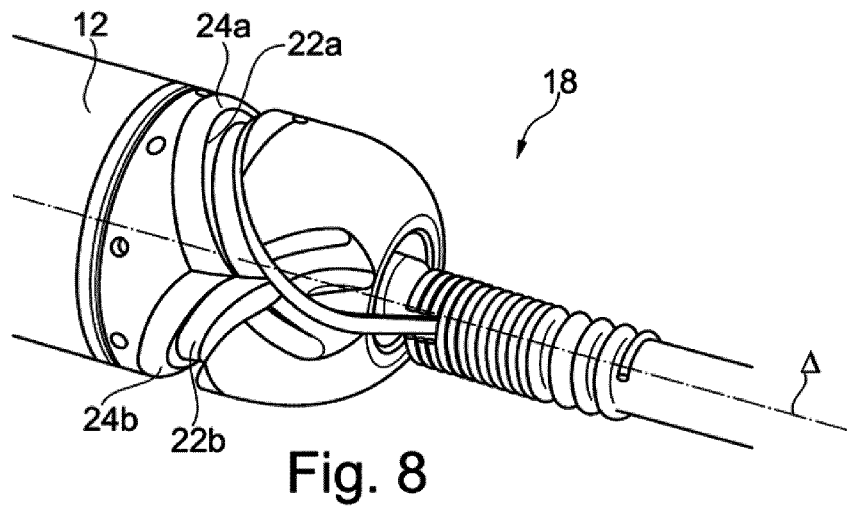
FIG. 8 is a detail view, in perspective, of the embodiment of FIG. 7, showing the proximal region of the capsule secured to the explantation accessory.

FIGS. 7 and 8 illustrate an alternative embodiment of the capsule as described above, including two diametrically opposed capture grooves 22a, 22b. These two grooves 22a, 22b define two respective regions 24a, 24b for reception of the lasso loop, which facilitates the capture by increasing the chances for hooking the loop.

Figure 9:
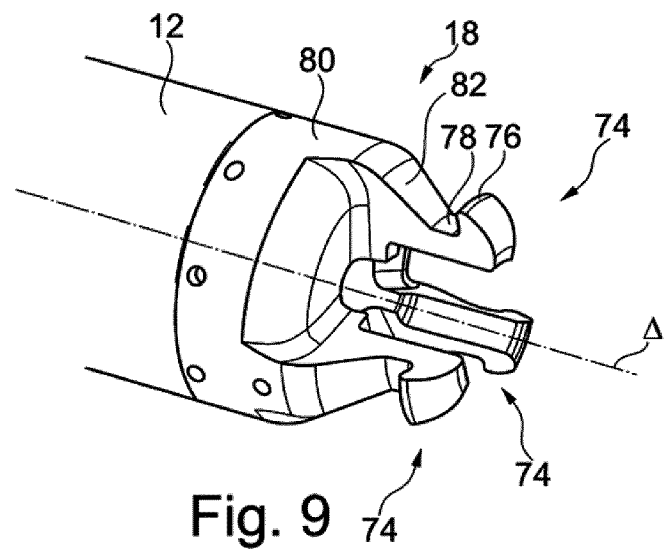
FIG. 9 illustrates an embodiment, wherein the capture member is constituted by a plurality of tie-down hooks.

FIG. 9 illustrates an alternative embodiment of the invention, wherein the capture member no longer has a groove, but has tie-down hooks 74, with, in the illustrated example, three identical tie-down hooks uniformly distributed at 120° around the axis Δ of the capsule. Each of the hooks 74 has a spout 76 directed axially outward in a radial direction and defining a reception area 78 for the loop closer to the axis Δ that the end of the spout 76. The reception area 78 is connected by a transition ramp 82 to region 80 extending the tubular body 12.

This configuration with this tie-down hooks has the advantage of facilitating the hold, by the loop of the lasso, of at least two hooks 74 during tightening of the lasso loop and during the decline of the latter towards the proximal end 18 of the capsule after the latter has been captured by the lasso.

Overall, it is emphasized that the assembly capsule/explantation accessory as just described has a number of significant advantages over the prior art:

a simple and reliable system, devoid of complex mechanism;

a method of operation close to the known practitioners' practices and used in other contexts;

the proximal portion of the capsule with the capture member (capture groove or tie down hooks) can be manufactured as an inexpensive molded component;

the unscrewing of the capsule does not need to operate redocking for unscrewing, that is to say it does not require mooring on the capsule of a large diameter system (of the same order as that of the capsule) which would be difficult to introduce and maneuver to the implantation site; and for explantation, the system does not require a venous path of large diameter as in the case of a redocking head.

The invention claimed is:

1. An intracardiac capsule assembly, the assembly comprising:
   an autonomous capsule comprising a tubular body having at a distal end a screw anchoring member adapted to penetrate tissue of a wall of an organ of a patient; and
   an explantation accessory, including:
   a catheter; and
   a flexible wire, having at a distal end a loop;
   wherein, in a proximal region, the capsule comprises a capture member adapted to receive the loop of the wire during a clamping thereof and to secure in traction and rotation the intracardiac capsule assembly formed by the catheter, the capsule, and the wire after clamping of the loop;
   wherein the capture member comprises at least one capture groove formed within the proximal end region of the capsule, each groove having a diameter less than a diameter of the tubular body and a contour, wherein the contour is an open contour comprising two ends which proximally open adjacent to an axial end point of the tubular body; and
   wherein a portion of the proximal end region of the capsule in which the at least one capture groove is formed has a diameter substantially the same as the diameter of the tubular body.

2. The assembly of claim 1, wherein the contour extends along a curvilinear outline oriented in an oblique plane relative to a central axis of the tubular body.

3. The assembly of claim 2, wherein the oblique plane according to which the curvilinear contour of each capture groove is oriented forms an angle of between 30° and 60° relative to the central axis of the tubular body.

4. The assembly of claim 1, wherein each capture groove is symmetrical with respect to a longitudinal axial plane of the tubular body.

5. The assembly of claim 1, wherein a profile of a cross section of each capture groove has on a proximal side an undercut angle.

6. The assembly of claim 1, wherein the profile of the cross section of each capture groove has on a distal side a gentle slope for connection to the tubular body.

7. The assembly of claim 1, comprising two symmetrical capture grooves diametrically opposed with respect to the central axis of the tubular body.

8. The assembly of claim 7, wherein the two symmetrical capture grooves have a width and depth greater than a diameter of the flexible wire loop.

9. The assembly of claim 1, wherein depth and width dimensions of the at least one groove are between 1 and 3 times a diameter of the flexible wire loop.

10. The assembly of claim 1, wherein the catheter is a reinforced catheter capable of transmitting a traction force and an axial torque from a proximal end to a distal end.

11. The assembly of claim 10, wherein the reinforced catheter carries at its distal end a specific tip comprising:
   a rigid distal tip portion, extending the catheter beyond the distal end thereof; and
   a proximal tip portion mounted on the catheter and elastically deformable so as to provide degrees of freedom in axial flexion for the rigid distal tip portion.

12. The assembly of claim 11, wherein the rigid distal tip portion comprises symmetrical notches for receiving the ends of the loop of the wire.

13. The assembly of claim 12, wherein the symmetrical notches have a width and depth greater than a diameter of the flexible wire loop.

14. The assembly of claim 11, wherein the specific tip is a helical spring comprising successively:
   a first series of turns surrounding the distal end of the catheter and forming the rigid distal tip portion;
   a second series of turns extending beyond the distal end of the catheter and forming the proximal tip portion; and
   a third series of turns at a free end of the spring with contiguous turns and symmetrical notches for receiving the ends of the loop of the wire.

15. The assembly of claim 1, wherein the assembly further comprises:
   a guidable catheter configured to receive the reinforced catheter with the wire introduced therein, this guidable catheter comprising at its distal end a tubular protective tip defining an inner volume dimensioned to accommodate the capsule after explantation.

16. The assembly of claim 1, wherein the wire is slidably movable in the catheter and the loop is configured to be clamped by gradual introduction of the loop in the catheter under an effect of a traction exerted on the flexible wire.

17. The assembly of claim 1, wherein the flexible wire loop has a diameter of between 10 mm and 30 mm.

18. The assembly of claim 1, wherein the tubular body as a diameter of 6 mm.

19. The assembly of claim 1, wherein the capsule has a length of about 25 mm.

20. The assembly of claim 1, wherein the flexible wire loop comprises a shape memory alloy such as nitinol.

* * * * *